US005532012A

United States Patent [19]
Balentine et al.

[11] Patent Number: 5,532,012
[45] Date of Patent: Jul. 2, 1996

[54] PROCESS FOR PREPARATION OF PURIFIED TEA COMPONENTS USING PRECONCENTRATION BY CREAM SEPARATION AND SOLUBILIZATION FOLLOWED BY MEDIUM PRESSURE CHROMATOGRAPHY AND/OR PREPARATIVE HPLC

[75] Inventors: Douglas A. Balentine, River Vale; Matthew E. Harbowy, New Brunswick, both of N.J.

[73] Assignee: Thomas J. Lipton Co., Division of Conopco, Inc., Englewood Cliffs, N.J.

[21] Appl. No.: 458,526

[22] Filed: Jun. 2, 1995

[51] Int. Cl.$^6$ .................................. A23F 3/18; A23F 3/20
[52] U.S. Cl. .................. 426/425; 426/429; 426/431; 426/435
[58] Field of Search ................... 426/435, 330.3, 426/597, 425, 429, 431

[56] References Cited

U.S. PATENT DOCUMENTS

| | | | |
|---|---|---|---|
| 4,004,038 | 1/1977 | Wickremasinghe | 426/422 |
| 4,048,344 | 9/1977 | Gasser et al. | 426/435 |
| 4,220,673 | 9/1980 | Strobel | 426/655 |
| 4,668,525 | 5/1987 | Creswick | 426/435 |
| 4,680,193 | 7/1987 | Lunder et al. | 426/271 |
| 4,748,033 | 5/1988 | Syfert et al. | 426/597 |
| 4,935,256 | 6/1990 | Tsai | 426/435 |
| 5,198,259 | 3/1993 | Hoogstad | 426/435 |

FOREIGN PATENT DOCUMENTS

| | | | |
|---|---|---|---|
| 688856 | 6/1964 | Canada | 426/435 |
| 0547370 | 6/1993 | European Pat. Off. . | |

OTHER PUBLICATIONS

STN Database Abstract. AN:94:31686 BIOSIS for Proceedings of the National Science Council Republic of China Part B Life Sciences 17(2). 1993 pp. 77–84, Authors: Xie et al.

STN Database Abstract. AN 1992:237791 CAPLUS for JP04020589 Dec. 4, 1992, Hara et al.

STN Database Abstract. AN 1994:294462 CAPLUS for CN 1076926A Feb. 24, 1993. Mao et al.

STN Database Abstract. AN 1994:433857 CAPLUS for CN 1074459A Jul. 21, 1993. SUN.

Powell, C. et al., "Tea Cream Formation: The Contribution of Black Tea Phenolic Pigments Determined by HPLC", *Journal of the Science of Food and Agriculture* (1993), vol. 63, Issue 4, pp. 77–86.

Yoshino, K. et al., "Antioxidative Effects of Black Tea Theaflavins and Thearubigin on Lipid Peroxidation of Rat Liver Homogenates Induced by text–butyl Hydroperoxide", *Biological Pharmaceutical Bulletin*, vol. 17,(1994), Issue 1, pp. 146–149.

Roberts, E., "The Phenolic Substances of Manufactured Tea", *J. Sci. Fd. Agric.*, Oct. 1963, vol. 14, pp. 700–705.

Smith, R., "Studies on the Formation and Composition of 'Cream' in Tea Infusions", *J. Sci. Fd. Agric.*, Sep. 1968, vol. 19, pp. 530–534.

Hazarika, M., "Studies on Thearubigin Pigments in Black Tea Manufacturing Systems", *J. Sci. Food Agric.*, 1984, vol. 35, pp. 1208–1218.

Nagalakshmi, S. et al., "Approaches to Decreaming of Black Tea Infusions by Solvent Decaffeination and Tannase Treatment", *J. Sci. Food Agric.*, 1985, vol. 22, No. 3, pp. 198–201.

Millen, D. et al., "Separation and Classification of the Brown Pigments of Aqueous Infusions of Black Tea", *J. Sci. Food Agric.*, May 1969, vol. 20, pp. 296–301.

Primary Examiner—Anthony J. Weier
Attorney, Agent, or Firm—James J. Farrell

[57] ABSTRACT

A method of obtaining selected tea polyphenol or theaflavin antioxidants in proportions reflective of those in natural tea is disclosed. The method employs a water solubilization of tea cream coupled with a mixed water/organic solvent extraction of the tea cream. The purified materials prepared are also disclosed.

11 Claims, No Drawings

PROCESS FOR PREPARATION OF PURIFIED TEA COMPONENTS USING PRECONCENTRATION BY CREAM SEPARATION AND SOLUBILIZATION FOLLOWED BY MEDIUM PRESSURE CHROMATOGRAPHY AND/OR PREPARATIVE HPLC

FIELD OF THE INVENTION

The present invention relates to a process for purifying and recovering selected polyphenol or theaflavin antioxidants from tea using preconcentration by cream separation and solubilization followed by medium pressure and high pressure liquid chromatography, as well as the composition containing the purified antioxidants in specific relative proportions representative of those found in natural teas.

BACKGROUND OF THE INVENTION

There is a great demand for water soluble or dispersible antioxidants in the food and health industries. Some of the most desirable antioxidants, polyphenols may be extracted, produced, recovered from various types of tea, such as green, black or oolong teas.

Utilizing black tea cream as a starting material for polyphenol isolation offers a number of distinct advantages. As a product of water extracts of tea leaf, the chemical constituents of cream are representative of the natural chemical constituents consumed as a beverage. The cream polyphenols have been analyzed for theaflavins and 'thearubigins' by C. Powell et al., in an article entitled "Tea Cream Formation: The Contribution of Black Tea Phenolic Pigments Determined by HPLC." *Journal of the Science of Food and Agriculture* (1993), Vol. 63, Issue 4, p. 77. However, this method is not suitable for separation of all of the components of black tea cream.

Recovery of certain types of antioxidants has been disclosed in EP 547 370 where tea leaves are extracted with water and then using water as the eluant are fractionated.

In an article by Kyoji Yoshino et al. reported in the *Biological Pharmaceutical Bulletin* Vol. 17, (1994) Issue 1, p. 146 entitled "Antioxidative Effects of Black Tea Theaflavins and Thearubigin on Lipid Peroxidation of Rat Liver Homogenates Induced by text-butyl Hydroperoxide", the antioxidative activities of theaflavins and thearubigins were studied and compared to standard antioxidants such as, for example, BHT and BHA.

The prior art in approaching antioxidant or polyphenol recovery from tea has usually employed water extraction and chromatographic separation but these methods have failed to prepare either pure or relatively pure mixtures of compounds in reasonably high yields with a reasonable number of extractions or fractionations. In addition, the final composition of the mixtures is completely different from the normal distribution of theaflavins or polyphenols present in natural tea or tea cream. Thus, the methods employed by the art have not been completely satisfactory.

Accordingly, it is an object of the present invention to produce mixtures of theaflavins or polyphenols which closely approximate the distribution of theaflavins or polyphenols in natural teas or tea extracts.

A further object of the invention is to produce these theaflavins by a relatively simple process which eliminates an excessive series of fractionations with chromatographic columns.

Yet a further object of the invention is to overcome or substantially eliminate some of the problems in the art.

It has now been discovered that many, if not all of the prior art difficulties, may be overcome by the instant invention which includes preparation of tea cream from black tea extracts, solubilization of the tea cream in an appropriate water/organic liquid solvent mixtures, separation of the organic solvent soluble polyphenols from the insoluble materials and recovery of selected polyphenols from the solution by extraction and/or chromatography whereby the polyphenols/theaflavins are recovered in 90% purity using a single chromatography step and very high theoretical yield and in about the same ratio that they are found in natural tea/natural tea cream.

SUMMARY OF THE INVENTION

The process for producing the polyphenols in high purity- and high yield generally involves producing tea cream by water extraction of tea leaf, then preparing and separating the cream from the supernatant liquid. The tea cream is resolubilized in heated water; then mixed in an organic liquid solvent which is miscible with water to allow resolubilization of the polyphenols. This liquid must be somewhat hydrophobic in character to dissolve the aggregated cream and hydrogen bond accepting in character to break the hydrogen bonds between the polyphenols and caffeine or other nitrogenous material in the cream. The liquid must also have a boiling point lower than water to facilitate removal. The mixture is then cooled, centrifuged and the solids precipitated out are removed. The solution containing the polyphenols is then further extracted by liquid/liquid extraction and/or chromatography.

One embodiment is as follows:

Black tea leaf is extracted to produce a concentrated tea extract, e.g., $\frac{1}{10}$, with boiling water. This extract is further concentrated under vacuum to produce an extract of high concentration, e.g., 10% solids. This solution is allowed to "cream" by holding at ca. 15° C. for greater than 30 minutes, followed by centrifugation to remove the cream from the supernate. The cream is then solubilized to regenerate a concentrated solution ca. 20% solids with boiling water, followed by addition of an approximately equal weight of a water-soluble solvent, e.g., acetone or alcohol. This solution is cooled to below room temperature and allowed to precipitate, followed by centrifugation to remove insoluble fines and other insoluble material.

This extract is suitable as a concentrated source of tea polyphenols upon drying, or may be used directly as a starting material for extraction and/or chromatography to prepare purified polyphenols.

DETAILED DESCRIPTION OF THE INVENTION

More particularly the invention procedure is as follows:
1. A method for producing a mixture of theaflavins or polyphenols closely approximating the natural mixture of said theaflavins or polyphenols existing in natural, untreated black tea or tea cream comprising:

(a) extracting black tea with water at a temperature of about 140° F. to 220° F. for about 2 to 10 minutes and a water to leaf ratio of about 10 to 1 to produce a tea solution containing about 2 to 4% by weight tea solids;

(b) concentrating said tea solution by vacuum to a concentration of about 6% to 20% by weight tea solids;

(c) cooling said concentrated tea solution-dispersion to a temperature of about 40° F. to 60° F. for about 30 to 90 minutes to form a suspension of tea cream representing about 10 to 40% of the original tea solids if untreated black tea is used;

(d) centrifuging said concentrated tea solution-dispersion to recover said tea cream;

(e) solubilizing said tea cream in water at a temperature of about 140° F. to 220° F. and a concentration of about 15 to 40% by weight of said tea cream to form a tea cream solution;

(f) mixing said tea cream solution with an organic liquid selected from the group consisting of acetone, ethanol, methanol, propanol, acetonitrile, mixtures thereof, or an organic liquid with a boiling point less than water and miscible in all proportions with water and having a hydrophobicity such that when mixed with water and polyphenols from said solubilized tea cream the polyphenols preferentially extract into said mixed liquid to solubilize tea cream polyphenols; in an amount of about 1 part organic liquid by weight to 9 parts water by weight to about 9 parts by weight of organic liquid to I part by weight of water, typically 1 part water to 1 part organic liquid;

(g) cooling said tea cream solution to a temperature of about 30° F. to 70° F. usually in excess of 15 minutes to precipitate out undesirable materials and form a soluble tea cream solution containing about 4 to 20% by weight tea cream solids;

(h) centrifuging or filtering to remove insoluble materials and to form a tea polyphenol solution;

(i) removing said organic liquid by heating and/or vacuum to recover polyphenols in aqueous solution in about the same ratio as said polyphenols occur in natural tea;

(j) performing liquid/liquid extraction using ethyl acetate, ethyl acetate and bicarbonate, methylene chloride, and/or chloroform to concentrate and further purify said polyphenol solution or to use directly;

(k) adding said tea polyphenol solution to a chromatography column packed with a separation medium selected from the group consisting of Sephadex LH-20, Toyopearl HW series, C-18 reversed-phase materials and mixtures thereof and eluting said tea polyphenol with a mixture of the following: acetic acid in water, water, acetone, acetonitrile, and or methanol, typically run as a gradient;

(l) collecting the last fraction(s) with strong absorbance at 450 nm, containing theaflavins;

(m) recovering said theaflavin whereby the ratio of theaflavin to theaflavin gallates relative to that of the starting mixture is from about 1:2 to 1:10 and in a purity of about 90% using only a single column and in 60% of theoretical yield.

The type of tea is not critical but can be any tea which produces cream. The extraction is done with deionized water to minimize dissolved minerals but could also be done with tap water. The water to leaf ratio for the extraction can be from 1 00 to 1 up to 5 to 1 and preferably is about 10 to 1. The temperature of extraction is about 140° F. to 220° F., preferably about 212° F. to simplify the procedure.

The extraction is carried out for a period of about 2 to 30 minutes and commercially may be carried out in a kettle at a temperature of about 195 ° F for about 10 minutes.

Once the tea is extracted, it is then cooled to a temperature of about 40° F. to 60° F. for about 30 to 90 minutes to produce cream in an amount of about 10% to 40% by weight. The cream is then separated from the supernatant by any convenient means, preferably centrifugation.

The centrifuged cream may be dried and stored for future use or may be used immediately. When used it is solubilized by dissolving in hot water.

The tea cream is preferably solubilized in an amount of about 15% to 40% in water at a temperature of about 140° F. to 220° F.

The tea cream solution is allowed to cool below the boiling point of the organic liquid solvent employed and is preferably solubilized in an amount of about 10% to 90% solvent in water.

While not wishing to be bound by theory, it is postulated that the liquid must break hydrogen bonds between the polyphenols and caffeine which normally exist in tea cream. Once this is accomplished, the liquid solvates the polyphenols while allowing contaminating material to precipitate in a flocculent mass. The liquid must also have some hydrophobic character to stabilize the hydrophobic regions of the polyphenols and assist in solubilization.

In order to remove it at a later stage, the liquid must have a boiling .point less than water. In addition, in order to have good contact within the mixed solution, the liquid must be miscible with water. The liquid may be acetone, isopropanol, ethanol, methanol or acetonitrile and is preferably acetone.

The amount of liquid added to the water/cream solution is about 1 part by weight water to 9 parts by weight liquid to about 9 parts by weight liquid to 1 part by weight water. Acetone, the preferred liquid, is shown in the FIGURE and it is clear that the solubility peaks at a 1 part water to 1 part acetone level but there is some solubility at both high and low levels.

A series of experiments were performed to determine the effective concentration range of acetone required to solubilize tea polyphenols in cream. All samples were made to a total weight of 550 g to insure a uniform experimental condition for each. For each data point, 50 g of tea cream was added to an appropriate amount of water at 70°–75 ° C. and homogenized using a high shear mixer. During mixing the suspension was left to cool to 40°–45 ° C., at which time the balance of acetone was added to the suspension. The mixture was homogenized for another 5–10 minutes and was then distributed in equal weights in four centrifuge bottles. The bottles were held overnight (≈16–19 hours) in a refrigerator kept at approximately 10°–15° C. The bottles were then placed in a 10° C. refrigerated centrifuge and spun at 10K×G for one hour. The supernate was drained, combined, and rotavapped to remove acetone. The remaining solution was weighed, followed by determination of dissolved solids. The weight of the liquid was multiplied by the percent solids and then divided by 50 g initial weight of cream to determine the percent resolubilization.

The FIGURE shows a plot of soluble solids (percent solubilization) versus the percent concentration of acetone in the final mixture. With no acetone, a small amount of solids return to solution (which are likely to represent soluble solids trapped in the liquid held by the cream during cream isolation). The amount of soluble solids rises dramatically at around 20% acetone, and at this concentration it appears to plateau. Above 40% acetone in solution, the graph begins to decline slightly. This is due to the decreasing concentration of water becoming less capable of providing the necessary hydration of the molecules in cream. Points above 65% were not analyzed because the quantity of water becomes insufficient to provide adequate solvation surface disabling good homogenization in the initial step of the experiment. For reference, 50 g of cream was homogenized in 500 g of acetone and the solids level in solution was analyzed, but this point should be considered separately due to the lack of water resuspension, which becomes experimentally inconsistent with the other points above the 65% acetone point. Thus, between about 60% and 90% the experimental conditions change by necessity and the last point in the FIGURE while it may not be completely accurate represents a good approximation.

Acetone, in addition to being a slightly hydrophobic solvent, is quite polar and is an excellent hydrogen-bond acceptor. It has been suggested under the hydrophobic effect hypothesis that at high concentrations of acetone, the acetone molecules aggregate around the hydrophobic surfaces and solubilize the polyphenols. This experiment demonstrates the profound hydrogen-bonding impact effect of acetone; even at low levels, the hydrogen-bond accepting capability of acetone dominates that of water and the intermolecular complexation, and breaks the aggregate's internal hydrogen bonds. However, at very high concentrations of acetone, the ability to solvate these molecules and bring them into the hydrogen bonding environment of water begins to be lost, because the acetone does not provide any hydrogen-bond accepting sites to solvate the hydrogen-bond-donating cream molecules.

The effect of acetone solubilization points to the importance of hydrogen bonding in the interactions of cream molecules with each other and with the bulk solution. Similar results are obtained with acetonitrile, which possesses a similar characteristic to acetone of hydrogen-bond accepting sites but no hydrogen-bond donors. Methanol, which is a much poorer hydrogen-bond acceptor but is of equivalent hydrophobicity, requires a higher mass percentage in water to achieve solubilization, and thus is disfavored compared to acetone.

Once the solvent-soluble tea cream solution has been prepared, the solution is cooled and centrifuged and filtered to remove any solids that precipitate. The temperature of cooling is about 40° F. to 60° F. The centrifugation takes place for about 20 to 90 minutes to separate the reasonable maximum amount of precipitate. The supernatant liquid then has the acetone or solvent soluble tea cream. This is concentrated by heat or vacuum and an aqueous suspension of cream polyphenols are recovered.

The polyphenols may be further concentrated for optimal extraction of theaflavins by extracting with any of the following: ethyl acetate, ethyl acetate and bicarbonate salts, methylene chloride, chloroform, or mixtures thereof.

The polyphenols in aqueous solution are then fractionated on a chromatography column. The column may be packed with Sephadex LH20, Toyopearl HW series, C-18 Reverse Phase material, or a combination of the above.

Having generally described various aspects of the present invention, the invention will now be more particularly described with reference to the following specific examples. All parts and proportions herein are by weight unless otherwise specified.

EXAMPLE 1

Black tea leaf was used from a number of sources, including World Blend, Lipton Tea Bag blend, BK82 (Kenya), BK81 (Assam), BK53 (Argentina), and BK44 (Brazil). Tea cream solutions isolated during the course of the experiments were kept refrigerated between chromatography runs.

Acetone, acetic acid and ethyl acetate (HPLC grade) were obtained from VWR Scientific and were used without further purification.

All water used was purified using reverse osmosis purification equipment followed by UV irradiation using HYDRO equipment (Picotech Research).

Sephadex LH-20 (Pharmacia) was obtained from Sigma Chemical and hydrated in 20% ethanol.

The first step involved preparation of a suitable tea cream extract. 150 g of black tea leaf (usually BK82) was extracted in 1500 ml boiling water to produce 1100 g extract at roughly 3.5% solids. This solution was concentrated using a Rotary Type Evaporator (Rotavapped) at 60°–75° C. under vacuum until the volume is ⅓ to ¼ of its original volume, leaving roughly 250 g of black tea extract at 10–15% solids. This sample was split into two fractions and held at 10°–15° C. for 30 minutes, then centrifuged at the same temperature for 30 minutes at 10,000×G in a Sorvall RC2-B centrifuge equipped with a GSA rotor head in 250 ml bottles.

The supernate was drained, leaving a pellet of tea cream. 60 g of boiling water (roughly half the original weight of each sample) was added to the pellet in the centrifuge bottle and homogenized using a Brinkmann Polytron PT-3000 equipped with a 1 cm diameter blade at 15,000–20,000 rpm. Acetone (roughly 60 g) was added to return the weight of each centrifuge bottle to the weight before the supernate was drained. A stringy, gelatinous precipitate formed on the addition of acetone. The samples were cooled to 10°–15° C. and centrifuged as before.

The 1/1 acetone/water supernate after centrifugation was a concentrated solution of theaflavins, "thearubigins", and flavonol glycosides, along with caffeine. This solution was suitable for direct injection onto Sephadex.

A Waters Prep-4000 HPLC equipped with an AP-5 50×600 mm glass column and a Waters 486 UV/VIS detector was used for the medium-pressure separation of cream. The column was packed by adding a slurry of the resin, A solution of 1% acetic acid in water was run at 15 ml/min. through the column to pressurize and settle the resin bed. More resin was added until the bed height reached the flow adjuster, which was set flush with the top of the resin bed. The detector was set to monitor at 450 nm, the absorption maximum for the theaflavins.

An injection of 60 ml of the acetone soluble tea cream in 50% acetone/water was made and UV response was recorded on a Waters 746 integrator. The mobile phases used were 1% acetic acid in water (buffer) and acetone, run on the following gradient:

0 min : 100% buffer 60 min : to 80% buffer/20% acetone over linear gradient 180 min : to 50% buffer over linear gradient 300 min : to 30% buffer over gradient curve 8

A single fraction was collected from approximately 280 minutes to 330 minutes, adjusted to coincide with the rise and fall of the detector response. The exact retention time varies by approximately ±10 minutes from run to run depending on the settling of the column during the run. Acetone was then removed from the fraction by rotavapping at 65° C. To remove acetic acid and some impurities the fraction was extracted 2 times 1/1 with ethyl acetate, rotavapped to near-dryness, and then resuspended in water. The sample was freeze dried overnight in a Virtis vacuum freeze drier using a final shelf temperature of 30° C. For each run, a sample was prepared at approximately 200 ppm for analysis on C-18 HPLC. In summary, a gradient of 0% to 25% of a 10% solution of glyme in acetonitrile vs. 1% acetic acid in water was run over a 45 minute run which separated all of the known compounds. Pure standards were used to quantitate wherever possible, and approximate extinction coefficients were used for peaks which could be assigned.

This method produced a sample of theaflavins free from known phenolic contaminants, approximately 30% theaflavins. This sample was redissolved in 50 ml of 50/50 acetone/water and injected onto a Waters PrepPak pre-packed preparative C-18 HPLC column, 47×300 mm. Using the same solvents as before, a linear gradient of 100% buffer to 50% buffer/50% acetone was followed over 120 minutes, monitoring at 450 nm. Two major peaks were found, one from 82 minutes to 102 minutes, the second from 103 minutes to 113 minutes. Each fraction was freeze-died and analyzed by C-18 HPLC as described previously.

In order to prepare a large quantity of purified material rapidly, the LH-20 portion of the procedure was run with theaflavins pre-purified initially on a preparative C-18 HPLC. A 60 ml injection of 1.25 g. of these crude theaflavins was repeatedly made and a fraction collected as before and freeze-dried. No further C-18 purification was necessary.

Table 1 summarizes the analytical data for each of the samples of freeze-dried material and indicates the current quantities of each material available as a dry powder.

Fractionation of tea cream into a sample containing theaflavins, theaflavic acids, and residual water has been achieved using a combination of LH-20 and C-18 chromatography. At each step of the procedure, the mass of the theaflavins is largely conserved, thus producing a finished mixture with concentrations of the four theaflavins at roughly "natural" ratios to one another.

Table 2 summarizes the average production per run of theaflavins using this procedure as run on current equipment and a scaled-up version of the procedure. Isolation of purified theaflavin will provide material for antioxidant studies and HPLC standardization.

A mixture of the four theaflavins, in >90% purity, was obtained from both tea cream and C-18 pre-purified theaflavins. Water, epitheaflavic acid 3-gallate and two theaflavin isomers were identified as the sole contaminants in theaflavins isolated from tea cream. Excellent mass balance was achieved in all the experiments.

TABLE 1

COMPOSITION OF PURIFIED BLACK TEA FRACTIONS

| FRACTION | % TF | % TFA | WEIGHT |
|---|---|---|---|
| Black Tea Extract Solids | 3.0% | 0.5% | |
| Black Tea Cream | 10.0% | 1.5% | 20.0 g |
| LH-20/extract purification | 25.0% | 4.0% | 1.50 g |
| C-18 workup after LH-20 | 91.0% | 4.0% | 0.05 g |
| C-18 workup of black tea | 51.0% | 1.5% | 0.10 g |
| LH-20 after C-18 workup | 90.5% | 4.0% | 2.00 g |

TABLE 2

ESTIMATED MAXIMUM YIELDS OF THEAFLAVINS

| COMPONENT | 5 × 60 cm. | 10 × 100 cm. |
|---|---|---|
| Theaflavins | 0.12–0.25 g | 0.6–1.5 g |
| Run Time | 6 hrs | 8 hrs |
| Acetone Used | 2 l | 13 l |
| Solvent Waste Created | 6 l | 40 l |

EXAMPLE 2

5g of acetone soluble BK82 cream (prepared as discussed in Example 1) freeze-dried solids were added to 100ml ethyl acetate and stirred for ten minutes. 100 ml of 5% Sodium Bicarbonate in water was then added and the mixture was stirred continuously for one hour. The solution was then allowed to separate in a 250 ml separatory funnel and the two layers separated. The aqueous fraction was re-extracted with 50 ml ethyl acetate. The ethyl acetate fractions were pooled and extracted with 50 ml water.

100 ml water was added to the ethyl acetate fraction and the solvent was stripped at 40° C. until bubbling ceased. 100 ml of acetone as added to dissolve insoluble particles and re-evaporated at 40° C. until bubbling ceased, leaving a transparent red solution. The solution was then freeze-dried.

The result of this was that 0.715 g of crude theaflavin was isolated. Analytical HPLC showed the mixture to be 24.17% caffeine, 21.39% theaflavins (3.55% TF, 5.95% TF3G, 3.75% TF3G, 8.14% TFDG), 12.05% catechins, and 0.15% theobromine. The mixture was isolated in 14.5 % yield from the acetone soluble BK82 cream solids. The mixture was free of theaflavic acids and other peaks which tend to coelute with the theaflavins and is therefore suitable for either C-18 or LH-20 chromatography for final purification.

A sample containing 21.37% of a mixture of the four theaflavins was prepared by partition of a sample of acetone-soluble cream between a solution of 5 % sodium bicarbonate and ethyl acetate (EtOAc). The procedure provides material suitable for further purification by LH-20 chromatography and should eliminate the need for a second chromatography column.

EXAMPLE 3

Typical run conditions are given below for isolation of theaflavins from black tea.

250 g of black tea leaf is extracted with 2500 g of boiling water for 10 minutes and the loose leaf removed by filtration. The extract is then concentrated using a rotary-type evaporator (rotavapped) at 60° C. to ¼ of its original volume, producing an extract of approximately 10–15% solids. The solution is then chilled to 15° C. for one hour and centrifuged at 10,000×G for 30 minutes. This produces approximately 50 g of a brown-white precipitate (cream).

50 g of the cream is redissolved in 250 ml of boiling water and homogenized. 250 ml of acetone is then added, rapidly causing a flocculent precipitate to form. The precipitate is removed by chilling to 15° C. for one hour and then centrifuging at 10,000×G for 30 minutes. The supernate is acetone soluble cream extract.

Acetone is removed from 500 ml of acetone soluble cream extract by rotary evaporation at 40° C., producing 250 ml of extract. 500 ml of ethyl acetate is added and allowed to stir for 10 minutes. 250 ml of a 2% solution of sodium bicarbonate is then added and the mixture is allowed to stir for one hour at room temperature. The solution is then allowed to separate into two phases (by centrifugation if necessary) and the aqueous phase is removed. The ethyl acetate phase is then re-extracted with 500 ml of 2% sodium chloride solution in water, and the aqueous phase is removed. The ethyl acetate phase is rotavapped to dryness and 1 00 ml of acetone is added to redissolve sample. 100 ml of water is added to produce 200 ml of a 50/50 acetone/water solution of theaflavin concentrate.

For theaflavin concentrate, 50 ml of solution is applied to the LH-20 column as described below. For total cream antioxidants, 75 ml of acetone soluble cream extract is applied.

HPLC chromatography is performed on a 5×300 column packed with LH-20 resin pressurized under a flow of 15 ml/min. of 1% acetic acid in water to about 200–300 psi. The following gradient is followed. 0 min. 100% of 1% acetic acid in water (buffer) 60 min. to 80% buffer/20% acetone over linear gradient 180 min. to 50% buffer/50% acetone over linear gradient 300 min. to 30% buffer/70% acetone over exponential curve Theaflavins normally are collected between 280 and 330 min., corresponding to an observed peak at 450 mn using a UV/Vis detector. All peaks at 350 nm are collected when using acetone soluble cream extract.

All collected fractions are freeze dried and labeled by peak number in order of elution.

Theaflavin produced from acetone soluble cream extract must be rechromatographed by C-18 chromatography on a Waters Prep-Pak, 47×300 nm, using a linear gradient from 100% buffer to 50% acetone/50% buffer over 120 minutes and a flow rate of 40 ml/min. The theaflavins are normally concentrated in the second major peak from 103–113 min. Theaflavins from theaflavin concentrate solution need not be rechromatographed.

0.25 g of pure theaflavin is produced from 50 ml of theaflavin concentrate. 0.2 g of theaflavin are produced from 75 ml of acetone soluble cream extract.

Sephadex LH-20-100 (Pharmacia) was packed into a Waters AP-5 50×300 mm glass HPLC column. A Waters Prep-4000 HPLC equipped with a variable wavelength UV detector set to 350 nm was used to determine collection start and stop times for each of the peaks.

The column was packed with a slurry of LH-20 resin pre-wetted in 50% ethanol. The flow rate of the prep HPLC was set to 15 ml/min., and the resin was allowed to compress under the pressure generated. After settling, more resin was slurried until the column achieved >26 cm in height, at which time the inlet adjustment was set so to place the inlet frit in contact with the resin bed.

To 100 g World Blend black tea (research blend lot 1 ), 500 g boiling water is added and allowed to stand, with occasional stirring, for five minutes. Acetone is added to bring the total weight to 1000 g. The leaf is then filtered off and the solution kept refrigerated until used. Solids are measured and recorded.

A 60 ml injection of the aqueous acetone tea extract is made and UV response is recorded on a Waters integrator. The mobile phases used are 1% acetic acid in water (buffer) and acetone, run on the following gradient: 0 min. 100% buffer 60 min. to 80% buffer/20% acetone over linear gradient 180 min. to 50% buffer/50% over linear gradient 300 min. : to 30% buffer over gradient curve 8

Acetone is removed from fractions by rotavapping at 65° C. and samples are freeze-dried. Each fraction is weighed and a sample is prepared at approximately 200 ppm for analysis on C-18 HPLC. In summary, a gradient of 0% to 25% of a 10% solution of glyme in acetonitrile vs. 1% acetic acid in water is run over a 45 minute run which separates all of the known compounds. Pure standards are used to quantitate wherever possible, and approximate extinction coefficients are used for peaks which could be assigned but for which no standard is available.

Sephadex LH-20 is an agarose-based gel-filtration media which has been modified with hydrophobic groups to produce a resin which separates partially on size-exclusion and partially on affinity. LH-20 has been demonstrated to separate theaflavins and "thearubigins". See for example: Brown, A, et al., "The Identification of the Thearubigins as Polymeric Proanthocyanidins", *Phytochemistry*, 8, (1969a) pp. 2333–2340 and Brown, A. et al.,, "Identification of the Thearubigins as Polymeric Proanthocyanidins", *Nature*, Vol. 221, (1969b), pp. 742–744. Traditional Sephadex separations are performed under low-pressure, low flow rate conditions and are run over long periods of time.

Excellent separation of a whole black tea brew into twelve fractions is achieved. These fractions are dried to powder form, and a 72% recovery of the mass of tea injected onto the column is achieved. Subsequent HPLC analysis of each of the fractions shows that black tea has been separated into two classes of flavonol glycosides, two classes of theaflavins, gallocatechins, cinnamic acids, caffeine, and two fractions which do not produce peaks on the analytical HPLC. The method is highly effective as an initial fractionation technique and can be used as a tool to facilitate the definition and quantitation of all the components found in black tea.

As above, LH-20 chromatography fractionates the Black Tea extract into twelve fractions absorbing at 350 nm. Fractions 5, 6 and 7 represent one peak and are combined to form peak 6. The remaining fractions each are unique and re-labelled as peaks. Peak 3 contains insufficient quantities of material to handle after freeze-drying and is not subjected to further analysis. Peaks 11 and 12 elute as bright red bands on LH-20 and are readily identified as theaflavins.

HPLC analysis is obtained for each of the fractions, and the corresponding UV spectra for each of the peaks observed. Gross features and the composition of each of the fractions can be partially determined from the analytical HPLC results.

Peak 11 consists primarily of theaflavin, representing 8.3% of this peak or 0.5% of the total tea solids. Theaflavin, isotheaflavin, theaflavin gallate, and epitheaflavic acid contribute 10% of this peak, or 0.61% of total tea solids.

Catechins represent 7.6% of peak 11, or 0.46% of total tea solids. The remainder of the mass of peak 11 does not appear on C-18 chromatography.

Peak 12 is primarily the theaflavin gallates, which represent 60.3% of the mass of peak 12, or 4.23% of total tea solids. The remainder of the mass of peak 12 does not appear on C-18 chromatography.

A summary of the composition of black tea by this method is given in Tables 3, 4 and 5.

TABLE 3

COMPOSITION OF WORLD BLEND REGULAR BLACK TEA EXTRACT SOLIDS

| | |
|---|---|
| Catechins | 6.73% |
| Theaflavins | 4.73% |
| Methylxanthines | 5.00% |
| Flavonol Glycosides | 2.37% |
| Phenolic Acids | 0.64% |
| TOTAL | 19.47% |
| Unknown | 80.53% |

(Percentages based upon isolated mass recovered)

TABLE 4

COMPOSITION OF TEA ASSOCIATION REGULAR BLACK TEA BY LH-20 PEAK

| | |
|---|---|
| Peak 1 unknowns | 0.92% |
| Peak 2 unknowns | 24.68% |
| Peak 3 unknowns | 2.40% |
| Peak 4 methylxanthines | 5.00% |
| Peak 4 unknowns | 2.82% |
| Peak 6 Cinnamic Acids | 0.43% |

TABLE 4-continued

COMPOSITION OF TEA ASSOCIATION REGULAR BLACK TEA BY LH-20 PEAK

| Peak 6 Flavonol Glycosides | 0.58% |
|---|---|
| Peak 6 unknowns | 5.60% |
| Peak 8 phenolic acids | 0.21% |
| Peak 8 Flavonol Glycosides | 0.76% |
| Peak 8 unknowns | 4.33% |
| Peak 9 catechins | 1.17% |
| Peak 9 Flavonol Glycosides | 1.03% |
| Peak 9 unknowns | 14.38% |
| Peak 10 catechins | 5.10% |
| Peak 10 unknowns | 17.53% |
| Peak 11 catechins | 0.46% |
| Peak 11 theaflavins | 0.61% |
| Peak 11 unknowns | 5.03% |
| Peak 12 theaflavins | 4.23% |
| Peak 12 unknowns | 2.79% |
| TOTAL | 99.95% |

(Percentages based upon isolated mass recovered)

TABLE 5

ESTIMATED MAXIMUM YIELDS OF COMPONENTS OF BLACK TEA FROM LH-20

| COMPONENT | 5 × 60 CM | 10 × 100 CM |
|---|---|---|
| Theaflavins | 0.12–0.25 g | 0.6–1.5 g |
| Flavonol Glycosides (FG) A | 0.01–0.02 g | 0.05–0.1 g |
| FG B | 0.01–0.03 g | 0.05–0.2 g |
| FG C | 0.02–0.04 g | 0.1–0.25 g |
| Cinnamic acids | 0.01–0.02 g | 0.05–0.1 g |
| Catechins | 0.10–0.25 g | 0.6–1.5 g |
| Run Time: | 6 hours | 8 hours |
| Acetone Used: | 2 l | 13 l |
| Solvent Waste Created: | 6 l | 40 l |

LH-20 chromatography under pressure represents a viable method for fractionating black tea into its constituent parts, easily separating theaflavins, flavonol glycosides, catechins, cinnamic acids, and "thearubigins" from one another.

The use of a pressurized column dramatically improves the performance of the LH-20 column with black tea. Run times are reduced, and the application of a controlled gradient allows better resolution than isocratic, gravity-fed methods. Reduced retention times should help lessen the chance of decomposition on column, which should result in better recovery of natural tea components.

EXAMPLE 4

World Blend freeze-dried black tea extract is used in all experiments. HPLC grade solvents are used to perform all extractions and chromatography. All water used is purified using RO purification followed by UV irradiation to deionize and prevent microbial contamination. Chromatography is performed using a Waters Delta-Pak 100Å C-18 47×100 mm Prep-pak module.

Freeze dried black tea extract is reconstituted to 10% wt/wt solids in boiling water. The solution is filled into 250 ml centrifuge bottles and chilled to below 15° C., holding at this temperature for at least one hour to allow formation of the freeze-dried black tea extract cream. The solution is centrifuged at 10K×G for 30 minutes to separate freeze-dried black tea extract cream from the supernate.

The bottles are decanted and the pellets are resuspended in a minimum amount of boiling water, ordinarily 25–50 ml per bottle. The resuspended freeze-dried black tea extract cream is combined into a large beaker or distributed equally among a minimum of 250 ml centrifuge bottles filled each to approximately 100 g. An equal volume of acetone is added to the pooled solution or to the individual bottles. The solutions are held chilled below 15° C. for at least one hour, but can be held indefinitely until continuing the workup.

This solution is then centrifuged at 10K×G for 60 minutes to separate the acetone insoluble freeze-dried black tea extract cream.

The supernate, or acetone soluble freeze-dried black tea extract cream, is combined and rotavapped at 40° C. under vacuum until the acetone is removed from solution, but without allowing the formation of precipitate. The solution is immediately transferred into a large container and stirred using a magnetic stirrer. An equal volume of ethyl acetate is added, and 1 g of Sodium Bicarbonate per 100 g of original freeze-dried black tea extract is allowed to dissolve into the stirring mixture. Stirring is allowed to continue for 60 minutes under brisk stirring, such that a vortex is observed in the liquid as well as swirling/mixing of the ethyl acetate and aqueous phases.

The ethyl acetate phase is allowed to settle and is separated. The aqueous phase is extracted additional times until the color of the ethyl acetate phase is significantly less red in color compared with the original phase. The ethyl acetate phase is then combined and washed with fresh water using about half the amount of water compared to ethyl acetate. The resulting ethyl acetate phase, i.e., the ethyl acetate extract of acetone soluble freeze-dried black tea extract cream, can be held refrigerated without a significant loss of theaflavins, but at no point should the process be stopped between centrifugation and the water wash.

The ethyl acetate phase is then stripped of solvent using a rotavap at 40° C. under vacuum. Before completion of the solvent removal, approximately 200 ml of methanol followed by 100 ml water/100 g original freeze-dried black tea extract is added through the rotavap addition pipe. The methanol is allowed to be removed under vacuum at 40° C., without allowing the solution to precipitate.

This solution, i.e., the ethyl acetate extract of acetone soluble freeze-dried black tea extract Cream in water, is then added to a separatory funnel and extracted at least four times with methylene chloride or chloroform to remove caffeine and a greenish material. The aqueous phase is then rotavapped gently to remove residual methylene chloride, and placed in freeze-dryer trays and freeze-dried. The resulting powder is theaflavin concentrate. This powder typically has a minimum theaflavin concentration of 27% and is typically less than 1% caffeine. Typical preparations can have as much as 35% theaflavin, depending on the quality of the freeze-dried black tea extract used in preparing the initial material, and can be increased to 45% by using a high-theaflavin leaf blend such as a high-quality Kenyan leaf, replacing the dissolved World Blend freeze dried black tea extract instant with the hot water extract of the leaf.

This material is chromatographed using a gradient chromatography system using C-18 packing material. 3.5 g of extract is dissolved in 30 g of 10% methanol solution. This solution is injected on-column and then chromatographed at a flow rate of 20 ml/min using a linear gradient over 120 minutes from 0% acetonitrile in water to 40% acetonitrile in water. Fractions which have a strong absorbance at 450 nm (usually between 65 and 90 minutes) are taken every 3 minutes and rotavapped to remove acetonitrile, followed by freeze-drying. Those fractions which contain concentrations of theaflavins greater than 85% are then pooled to form a combined mixture, called the theaflavin isolate. This fraction is typically in excess of 92% theaflavins.

As a result of the methods of Example 4, two purified materials, a Theaflavin Isolate and a Theaflavin Concentrate, were prepared using standard extractions, with one chromatography step needed to prepare the theaflavin isolate.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method for producing a mixture of theaflavins closely approximating the natural mixture of said theaflavins existing in tea cream comprising:
   (a) obtaining said tea cream from black tea;
   (b) solubilizing said tea cream in water at a temperature of about 140° F. to 220° F. and a concentration of about 15 to 40% by weight of said tea cream to form a tea cream solution;
   (c) mixing said tea cream solution with an organic liquid to form a mixed liquid solution, said organic liquid having a boiling point less than water, being miscible in all proportions with water and having a hydrophobicity such that when mixed with water and theaflavins from said solubilized tea cream, the theaflavins preferentially extract into said mixed liquid to solubilize said tea cream theaflavins, said organic liquid being present in an amount of about 1 part by weight to 9 parts water by weight in said mixed liquid to about 9 parts by weight of organic liquid to 1 part by weight of water, in said mixed liquid;
   (d) cooling said mixed liquid solution to a temperature of about 30° F. to 70° F. to precipitate out undesirable materials;
   (e) removing insoluble materials to form a solution containing about 4 to 20% by weight tea cream solids and containing said theaflavins.

2. A method as defined in claim 1 wherein said organic liquid is selected from the group consisting of acetone, ethanol, methanol, propanol, acetonitrile, and mixtures thereof.

3. A method as defined in claim 2 wherein said organic liquid is acetone or acetonitrile or a mixture thereof.

4. A method for producing a mixture of theaflavins closely approximating the natural mixture of said theaflavins existing in tea cream comprising:
   (a) obtaining said tea cream from black tea;
   (b) solubilizing said tea cream in water at a temperature of about 140° F. to 220° F. and a concentration of about 15 to 40% by weight of said tea cream to form a tea cream solution;
   (c) mixing said tea cream solution with an organic liquid to form a mixed liquid solution, said organic liquid having a boiling point less than water, being miscible in all proportions with water and having a hydrophobicity such that when mixed with water and theaflavins from said solubilized tea cream, the theaflavins preferentially extract into said mixed liquid to solubilize said tea cream theaflavins, said organic liquid being present in an amount of about 1 part by weight to 9 parts water by weight in said mixed liquid to about 9 parts by weight of organic liquid to 1 part by weight of water, in said mixed liquid;
   (d) cooling said mixed liquid solution to a temperature of about 30° F. to 70° F. to precipitate out undesirable materials;
   (e) removing insoluble materials to form a solution containing about 4 to 20% by weight tea cream solids and containing said theaflavins;
   (f) removing said organic liquid to recover theaflavins in aqueous solution in about the same ratio as said theaflavins occur in natural tea.

5. A method as defined in claim 1 further comprising evaporating the water from said aqueous theaflavin solution and recovering dried theaflavins.

6. A method for producing a mixture of theaflavins closely approximating the natural mixture of said theaflavins existing in tea cream comprising:
   (a) obtaining said tea cream from black tea;
   (b) solubilizing said tea cream in water at a temperature of about 140° F. to 220° F. and a concentration of about 15 to 40% by weight of said tea cream to form a tea cream solution;
   (c) mixing said tea cream solution with an organic liquid to form a mixed liquid solution, said organic liquid having a boiling point less than water, being miscible in all proportions with water and having a hydrophobicity such that when mixed with water and theaflavins from said solubilized tea cream, the theaflavins preferentially extract into said mixed liquid to solubilize said tea cream theaflavins, said organic liquid being present in an amount of about 1 part by weight to 9 parts water by weight in said mixed liquid to about 9 parts by weight of organic liquid to 1 part by weight of water, in said mixed liquid;
   (d) cooling said mixed liquid solution to a temperature of about 30° F. to 70° F. to precipitate out undesirable materials;
   (e) removing insoluble materials to form a solution containing about 4 to 20% by weight tea cream solids and containing said theaflavins;
   (f) removing said organic liquid by heating and/or vacuum to recover theaflavins in aqueous solution in about the same ratio as said theaflavins occur in natural tea;
   (g) performing liquid/liquid extraction using an extraction media selected from the group consisting of ethyl acetate; ethyl acetate and bicarbonate; methylene chloride; methyl isobutyl ketone; chloroform and mixtures thereof to concentrate said theaflavin solution.

7. A method as defined in claim 6 wherein the liquid/liquid extraction of said step (g) is performed in series employing first ethyl acetate and then a mixture of ethyl acetate and bicarbonate.

8. A method as defined in claim 6 further comprising:
   (h) adding said concentrated theaflavin solution to a chromatography column packed with a separation medium and eluting said theaflavin with a mixture selected from the group consisting of acetic acid in water, water, acetone, acetonitrile, and methanol, run as a gradient to form fractions of said solution;
   (i) collecting the last fractions from said solution, said fractions having a strong absorbance at 450 nm and containing said theaflavins;
   (j) recovering said theaflavins whereby the ratio of said theaflavin to theaflavin gallates relative to that of the starting mixture is from about 1:2 to 1:10 and in a purity of about 90% using only a single column and in 60% of theoretical yield.

9. A method as defined in claim 7 further comprising:
(h) adding said concentrated theaflavin solution to a chromatography column packed with a separation medium and eluting said tea polyphenol with a mixture selected from the group consisting of acetic acid in water, water, acetone, acetonitrile, and methanol, run as a gradient to form fractions of said solution;
(i) collecting the last fractions from said solution, said fractions having a strong absorbance at 450 nm and containing said theaflavins;
(j) recovering said theaflavins whereby the ratio of said theaflavin to theaflavin gallates relative to that of the starting mixture is from about 1:2 to 1:10 and in a purity of about 90% using only a single column and in 60% of theoretical yield.

10. A method as defined in claim 7 further comprising drying the concentrated theaflavin solution.

11. A method for producing a mixture of theaflavins closely approximating the natural mixture of said theaflavins existing in tea cream comprising;
(a) obtaining said tea cream from black tea;
(b) solubilizing said tea cream in water at a temperature of about 140° F. to 220° F. and a concentration of about 15 to 40% by weight of said tea cream to form a tea cream solution;
(c) mixing said tea cream solution with an organic liquid to form a mixed liquid solution, said organic liquid having a boiling point less than water, being miscible in all proportions with water and having a hydrophobicity such that when mixed with water and theaflavins from said solubilized tea cream, the theaflavins preferentially extract into said mixed liquid to solubilize said tea cream theaflavins, said organic liquid being present in an amount of about 1 part by weight to 9 parts water by weight in said mixed liquid to about 9 parts by weight of organic liquid to 1 part by weight of water, in said mixed liquid;
(d) cooling said mixed liquid solution to a temperature of about 30° F. to 70° F. to precipitate out undesirable materials;
(e) removing insoluble materials to form a solution containing about 4 to 20% by weight tea cream solids and containing said theaflavins;
(f) adding said theaflavin solution to a chromatography column packed with a separation medium and eluting said theaflavin with a mixture selected from the group consisting of acetic acid in water, water, acetone, acetonitrile, and methanol, run as a gradient to form fractions of said solution;
(g) collecting the last fractions from said solution, said fractions having a strong absorbance at 450 nm and containing said theaflavins;
(h) recovering said theaflavins whereby the ratio of said theaflavin to theaflavin gallates relative to that of the starting mixture is from about 1:2 to 1:10 and in a purity of about 90% using only a single column and in 60% of theoretical yield.

* * * * *